(12) United States Patent
Atkinson et al.

(10) Patent No.: US 8,415,614 B2
(45) Date of Patent: *Apr. 9, 2013

(54) ION MOBILITY SPECTROMETER COMPRISING TWO DRIFT CHAMBERS

(75) Inventors: Jonathan Richard Atkinson, Watford (GB); Alastair Clark, Dunstable (GB); Stephen John Taylor, Hyde Heath (GB)

(73) Assignee: Smiths Detection—Watford Limited, Watford, Hertfordshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/205,219

(22) Filed: Aug. 8, 2011

(65) Prior Publication Data

US 2011/0291000 A1  Dec. 1, 2011

Related U.S. Application Data

(63) Continuation of application No. 12/529,247, filed on Aug. 31, 2009, now Pat. No. 7,994,475.

(30) Foreign Application Priority Data

Mar. 3, 2007 (GB) .................................. 0704137.9

(51) Int. Cl.
*B01D 59/44* (2006.01)
(52) U.S. Cl.
USPC ........... 250/282; 250/281; 250/285; 250/288; 250/290; 250/292

(58) Field of Classification Search .................. 250/281, 250/282, 285–288, 290, 292
See application file for complete search history.

(56) References Cited

U.S. PATENT DOCUMENTS

| | | |
|---|---|---|
| 5,227,628 A | 7/1993 | Turner |
| 6,100,521 A | 8/2000 | Doering et al. |
| 6,225,623 B1 | 5/2001 | Turner et al. |
| 7,820,962 B2 | 10/2010 | Wynn et al. |
| 7,994,475 B2 * | 8/2011 | Atkinson et al. .............. 250/292 |
| 2002/0088936 A1 | 7/2002 | Breach et al. |
| 2007/0040111 A1 | 2/2007 | Jill et al. |
| 2009/0174412 A1 | 7/2009 | Atkinson et al. |
| 2010/0230588 A1 | 9/2010 | Atkinson et al. |

FOREIGN PATENT DOCUMENTS

| | | |
|---|---|---|
| EP | 0027748 | 4/1981 |
| EP | 0509171 | 10/1992 |
| EP | 0692712 | 1/1996 |
| GB | 2228139 A | 8/1990 |
| WO | WO 2006123107 | 11/2006 |

* cited by examiner

*Primary Examiner* — Michael Maskell
(74) *Attorney, Agent, or Firm* — Reinhart Boerner Van Deuren s.c.

(57) ABSTRACT

An ion mobility spectrometer has two drift chambers and a common, doped reaction region. Each drift chamber includes an ion modifier, such as one that fragments the doped ions by a high electrical field. One of the drift chambers is doped and the other is undoped. In this way, the dopant adducts are removed by the modification process but then recombine with dopant only in the doped chamber so that different outputs are produced by the two drift chambers.

20 Claims, 1 Drawing Sheet

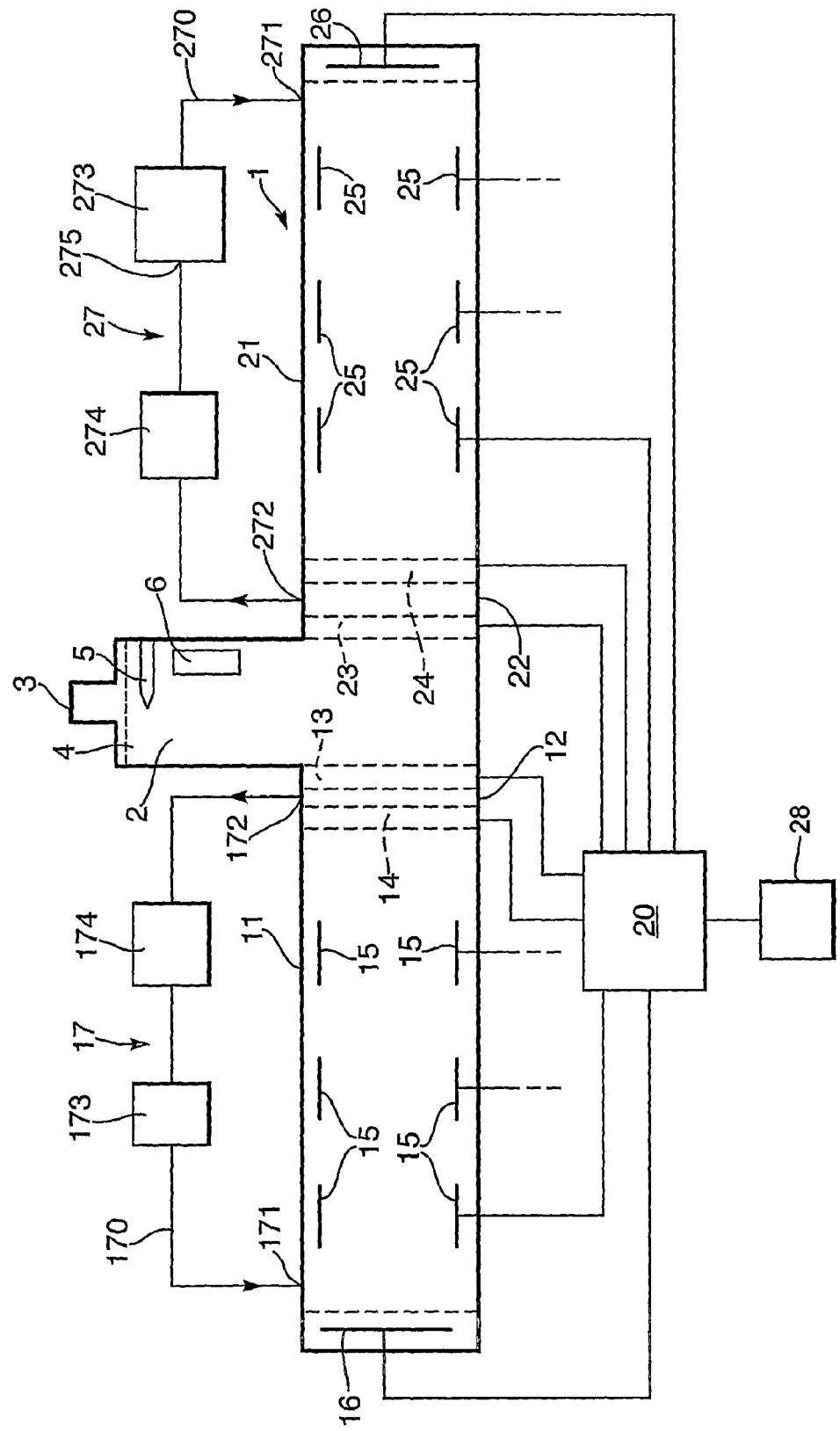

ION MOBILITY SPECTROMETER COMPRISING TWO DRIFT CHAMBERS

CROSS REFERENCE TO RELATED APPLICATION

This patent application is a continuation of U.S. patent application Ser. No. 12/529,247, filed on Aug. 31, 2009, now U.S. Pat. No. 7,994,475, issued on Aug. 9, 2011, entitled "Ion Mobility Spectrometers," which patent application is assigned to the assignee of the present invention and which patent application is hereby incorporated herein by reference in their entirety.

BACKGROUND OF THE INVENTION

Field of the Invention

This invention related to ion mobility spectrometers of the kind having two drift chambers and a common reaction region.

Ion mobility analysis is a commonly used technique for detecting the presence of explosives, hazardous chemicals and other vapors. An ion mobility spectrometer (IMS) typically includes a detector cell to which a sample of air containing a suspected substance or analyte is continuously supplied as a gas or vapor. The cell operates at or near atmospheric pressure and contains electrodes energized to produce a voltage gradient along the cell. Molecules in the sample of air are ionized, such as by means of a radioactive source, an ultraviolet (UV) source, or by corona discharge, and the ionized molecules are admitted into the drift region of the cell by an electrostatic gate at one end. The ionized molecules drift to the opposite end of the cell at a speed that is dependent upon the mobility of the ions. By measuring the time of flight along the cell it is possible to identify the ions.

In order to improve detection, it is common practice to add a dopant substance to the analyte substance in order to distinguish between the analyte substance and an interferent substance producing a similar spectral output. The dopant is selected to combine with the substance of interest so that an identifiable pair of spectral peaks are produced in respect of the undoped and doped analyte substance. The dopant is also selected so that it does not combine with the interferent substance, or so that it combines with the interferent substance in a manner that produces a readily distinguishable output different from the output of the substance of interest.

Dopant adducts can be removed from certain ions in an ion modifier, such as of the kind where the ions are modified by the application of a high field. This is only effective, however, if the region of the ion modifier is free of dopant, since otherwise recombination may occur. Alternatively, dopant adducts can be removed by raising the temperature. The removal of the dopant adducts, however, occurs progressively all the way along the drift region, so rather than producing sharp undoped and doped monomer peaks what is produced are two misshapen peaks with bridging between them.

It is accordingly desirable to provide an alternative ion mobility spectrometer.

SUMMARY OF THE INVENTION

According to one aspect of the present invention there is provided an ion mobility spectrometer of the above-specified kind, characterized in that the reaction region is doped so that all analyte samples are exposed to doping prior to being supplied to respective ones of a pair of drift chambers, wherein each drift chamber includes an ion modifier, with one of the drift chambers being doped and the other one of the drift chambers being undoped. When doped analyte ions are subject to ion modification in the undoped drift chamber, the dopant adducts are removed, but when doped analyte ions are subject to ion modification in the doped drift chamber, analyte ions combine with dopant in the drift chamber, such that different outputs are provided from the two drift chambers.

At least one ion modifier may include an arrangement for establishing a high electrical field sufficient to fragment the ions. Alternatively, at least one ion modifier may be effective to raise the temperature. The two drift chambers are preferably arranged back-to-back. The dopants in the reaction region and in the doped drift chamber may be the same, or they may be different. The doped chamber may be doped by means of a doped molecular filter. The spectrometer may be arranged to initiate ion modification in response to the detection of a peak corresponding to a known interferent such that dopant adducts are removed in the undoped chamber only.

DESCRIPTION OF THE DRAWINGS

An ion mobility spectrometer that is constructed and operated according to the present invention will now be described, by way of example, with reference to the accompanying drawing, which is a schematic diagram of an exemplary ion mobility spectrometer.

DETAILED DESCRIPTION OF THE PREFERRED EMBODIMENT

The spectrometer has a tubular drift cell assembly 1 with a centrally-arranged reaction region or reaction chamber 2 having an inlet 3 forming an inverted T shape. The spectrometer operates at, or close to, atmospheric pressure. The inlet 3 opens into the upper end of the reaction chamber 2 via a selective barrier 4, such as a membrane, pinhole, or the like. The reaction chamber 2 includes some conventional ionization means, shown as a corona ionization point 5, but which could instead be of any alternative form, such as a radioactive source or a UV photoionization source. The reaction chamber 2 also includes a conventional doping means 6 such as a heated supply of a dopant chemical contained in an absorbant material that is arranged and configured to release the dopant chemical at a slow rate.

The lower end of the reaction chamber 2 communicates with two cells or drift chambers 11 and 21 which are arranged axially and back to back with respect to each other so that their respective inlet ends 12 and 22 are disposed centrally with respect to the lower end of the reaction chamber 2 and open into the reaction chamber 2. The drift chamber 11 is shown on the left in the FIGURE, and the drift chamber 21 is shown on the right in the FIGURE. This configuration of twin IMS drift chambers is shown in U.S. Pat. No. 5,227,628, to Turner, which patent is hereby incorporated herein by reference. Each of the drift chambers 11 and 21 includes a conventional electrostatic gate 13 and 23, respectively, by which ions from the reaction chamber 2 are admitted into or excluded from the drift chambers 11 and 21, respectively. Operation of the electrostatic gates 13 and 23 is controlled by a processing/control unit 20.

Downstream of the electrostatic gates 13 and 23 in the drift chambers 11 and 21, respectively, is mounted an ion modifier means in the form of a pair of parallel electrode grids 14 and 24, respectively, which extend laterally of the ion flow path, which is axially along each of the drift chambers 11 and 21. The construction of the electrode grids 14 and 24 is such as to allow ions to pass freely through them and, in this respect, the electrode grids 14 and 24 are preferably made from a mesh of electrically-conductive wires with spaces between them through which the ions can flow. The electrode grids 14 and 24 are connected to the processing/control unit 20, which is operable to apply a high voltage between the electrode grids 14 and 24 that is sufficient to modify the nature of any ions in the space between the electrode grids 14 and 24, such as by fragmentation of the ions.

An additional effect of this high field is to remove the dopant adducts from the ions. Each of the drift chambers 11 and 21 has several drift electrodes 15 and 25, respectively, of the usual kind, that are spaced along the drift chambers 11 and 21, respectively, and are connected to the processing/control unit 20, which applies a voltage to the drift electrodes 15 and 25 to establish potential gradients along each of the drift chambers 11 and 21, respectively, which is effective to draw the ions to the far ends of the drift chambers 11 and 21. The ion modifiers could take various different forms and could, for example, include a heater effective to raise the temperature of the ions sufficiently to modify them.

At the far end of each of the drift chambers 11 and 21, detector or collector plates 16 and 26, respectively, are located in line with the ion flow paths so as to receive the ions passed along the lengths of the respective drift chambers 11 and 21. Each of the collector plates 16 and 26 is connected with the processing/control unit 20 so as to produce an output spectrum representative of the ions that incident on the collector plates 16 and 26, in the usual way. The outputs from the collector plates 16 and 26 are provided to a display 28 or other utilization means.

Air is circulated along both of the cells 11 and 21 in opposition to the ion flow direction by respective, separate air flow systems 17 and 27. The air flow system 27 for the drift chamber 21 shown on the right side in the FIGURE comprises a flow path 270 having an outlet 271 into the drift chamber 21 adjacent the collector plate 26. An inlet 272 of the flow path 270 is located adjacent the electrostatic gate 23. Air is caused to flow along the flow path 270 by means of a pump 273 having a molecular filter unit 274 connected in line between the flow path inlet 272 and an inlet 275 of the pump 273. Air is, therefore, circulated to flow from right to left (as shown in the FIGURE) along the cell 21 and is dried and cleaned by the action of the molecular filter unit 274.

The air flow system 17 connected with the drift chamber 11 shown on the left side in the FIGURE is similar, and has a pump 173 and a molecular filter 174 connected to provide a circulating flow of air along the drift chamber 11 from left to right as shown in the FIGURE, against the flow of ions. The flow system 17 of the drift chamber 11, however, differs from that of the drift chamber 21 in that the molecular filter 174 of the drift chamber 11 is impregnated with a dopant chemical so that the air circulating in the drift chamber 11 is continuously doped. There are alternative arrangements by which the drift chamber 11 could be doped. The drift chamber 21 lacks any such doping so it is undoped, in contrast with the doped nature of the drift chamber 11.

In operation, the analyte sample vapor is admitted to the drift cell assembly 1 via the inlet 3 and the barrier 4, and it is doped and ionized in the reaction chamber 2. The resultant ions then move, such as by an electric field produced by charged plates (not shown), towards the inlet ends 12 and 22 of the drift chambers 11 and 21, respectively. The doped ions are admitted in a timed fashion by the electrostatic gates 13 and 23 under control of the processing/control unit 20, and enter the respective drift chambers 11 and 21 in equal numbers. In normal operation, with the ion modifier electrostatic grids 14 and 24 unenergized, the doped ions move along the respective drift chambers 11 and 21 to the collector plates 16 and 26, respectively, and produce substantially identical responses at the processing/control unit 20, which responses are combined to produce an output indicative of the analyte substances.

If, however, the output includes a peak for which there is a known interferent, the ion modifier electrode grid 14 and/or the ion modifier electrode grid 24 in either one or both of the drift chambers 11 and/or 21, respectively, is turned on. The effect of this in the undoped, drift chamber 21 (shown on the right side of the FIGURE) is to remove dopant adducts in its undoped drift region, and these undoped ions continue in their passage along the drift chamber 21 to the detector plate 26. It may also cause fragmentation or other changes in the ion chemistry.

In the doped, drift chamber 11 (shown on the left side of the FIGURE), however, although initially the ion modifier 14 is effective to remove the dopant adducts from the ions, the ions rapidly recombine with the dopant substance flowing along the drift chamber 11. The dopant in the drift chamber 11 may be the same as or different from the dopant used in the reaction chamber 2. The ion modifier 14, however, may be effective to alter the ion chemistry of the doped ions.

It can be seen, therefore, that the output from the two drift chambers 11 and 21 will be different. The output response produced by the analyte substance of interest and its interferent will generally be different in one or both of the cells when the ion modifier is turned on. By characterizing the apparatus before use with the analyte substance and its interferent, it is, therefore, possible to distinguish between the substance and its interferent.

Although the foregoing description of the dual drift chamber ion mobility spectrometer the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

What is claimed is:

1. A method of operating an ion mobility spectrometer comprising:
   exposing analyte samples to doping in a reaction region;
   providing doped analyte ions from the reaction region to each of two drift chambers;
   doping one of the drift chambers, the other drift chamber being undoped; and
   subjecting doped analyte ions entering each of the drift chambers to an ion modifier in each of the drift chambers, such that when doped analyte ions are subject to ion modification in the undoped drift chamber, the dopant adducts are removed, but when doped analyte ions are subject to ion modification in the doped drift chamber, analyte ions combine with dopant in the doped drift chamber, such that different outputs are provided from the two drift chambers.

2. A method as defined in claim 1, wherein at least one ion modifier includes an arrangement for establishing a high electrical field sufficient to fragment ions.

3. A method as defined in claim 1, wherein at least one ion modifier is effective to raise the temperature.

4. A method as defined in claim 1, wherein the two drift chambers are arranged back to back.

5. A method as defined in claim 1, wherein the dopants in the reaction region and in the doped drift chamber are the same.

6. A method as defined in claim 1, wherein the dopants in the reaction region and in the doped drift chamber are different.

7. A method as defined in claim 1, wherein the doped drift chamber is doped by means of a doped molecular filter.

8. A method as defined in claim 1, wherein the spectrometer is arranged and configured to initiate ion modification in response to detection of a peak corresponding to a known interferent such that dopant adducts are removed in the undoped drift chamber only.

9. An ion mobility spectrometer comprising:
    a doped reaction region exposing analyte samples to doping;
    two drift chambers each of which is supplied with doped analyte ions from the reaction region, one of the drift chambers being doped, the other drift chamber being undoped; and
    an ion modifier in each of the drift chambers, wherein doped analyte ions entering each of the drift chambers are subjected to the ion modifier to remove dopant adducts, wherein analyte ions in the doped drift chamber combine with dopant in the doped drift chamber, whereby different outputs are provided from the two drift chambers.

10. An ion mobility spectrometer as defined in claim 9, wherein at least one ion modifier includes an arrangement for establishing a high electrical field sufficient to fragment ions.

11. An ion mobility spectrometer as defined in claim 9, wherein at least one ion modifier is effective to raise the temperature.

12. An ion mobility spectrometer as defined in claim 9, wherein the two drift chambers are arranged back to back.

13. An ion mobility spectrometer as defined in claim 9, wherein the dopants in the reaction region and in the doped drift chamber are the same.

14. An ion mobility spectrometer as defined in claim 9, wherein the dopants in the reaction region and in the doped drift chamber are different.

15. An ion mobility spectrometer as defined in claim 9, wherein the doped drift chamber is doped by means of a doped molecular filter.

16. An ion mobility spectrometer as defined in claim 9, wherein the spectrometer is arranged and configured to initiate ion modification in response to detection of a peak corresponding to a known interferent such that dopant adducts are removed in the undoped drift chamber only.

17. A method of operating an ion mobility spectrometer comprising:
    exposing analyte samples to doping in a reaction region;
    providing doped analyte ions from the reaction region to each of two drift chambers;
    doping one of the drift chambers, the other drift chamber being undoped; and
    subjecting doped analyte ions entering each of the drift chambers to an ion modifier in that chamber to remove dopant adducts, wherein analyte ions in the doped drift chamber combine with dopant in the doped drift chamber, whereby different outputs are provided from the two drift chambers.

18. A method as defined in claim 17, wherein at least one ion modifier includes an arrangement for establishing a high electrical field sufficient to fragment ions.

19. A method as defined in claim 17, wherein the two drift chambers are arranged back to back.

20. A method as defined in claim 17, wherein the spectrometer is arranged and configured to initiate ion modification in response to detection of a peak corresponding to a known interferent such that dopant adducts are removed in the undoped drift chamber only.

* * * * *